(12) United States Patent
Matsumoto et al.

(10) Patent No.: US 6,456,787 B1
(45) Date of Patent: Sep. 24, 2002

(54) EYE FUNDUS CAMERA

(75) Inventors: Kazuhiro Matsumoto, Tochigi; Hiroshi Nishihara, Kanagawa, both of (JP)

(73) Assignee: Canon Kabushiki Kaisha, Tokyo (JP)

( * ) Notice: Subject to any disclaimer, the term of this patent is extended or adjusted under 35 U.S.C. 154(b) by 25 days.

(21) Appl. No.: 09/718,418

(22) Filed: Nov. 24, 2000

(30) Foreign Application Priority Data

Nov. 26, 1999  (JP) .......................................... 11-336752

(51) Int. Cl.[7] ................................................ A61B 3/14
(52) U.S. Cl. ...................... 396/18; 396/110.6; 351/206; 351/211
(58) Field of Search .................. 396/106, 18; 351/206, 351/210, 211, 213, 221

(56) References Cited

U.S. PATENT DOCUMENTS

| 4,436,388 A | * | 3/1984 | Takahashi et al. | ........... 396/106 |
| 4,820,037 A | | 4/1989 | Kohayakawa et al. | ...... 351/211 |
| 4,848,896 A | | 7/1989 | Matsumoto | ................. 351/211 |
| 4,952,049 A | | 8/1990 | Matsumoto | ................. 351/211 |
| 5,233,372 A | | 8/1993 | Matsumoto | ................. 351/221 |
| 5,430,509 A | * | 7/1995 | Kobayashi | ................. 351/206 |
| 5,455,644 A | | 10/1995 | Yazawa et al. | ............. 351/206 |
| 5,565,938 A | * | 10/1996 | Hanamura et al. | .......... 351/206 |
| 5,847,805 A | | 12/1998 | Kohayakawa et al. | ...... 351/210 |
| 6,325,511 B1 | * | 12/2001 | Mizuochi | .................... 351/206 |

FOREIGN PATENT DOCUMENTS

JP         11-225972          8/1999

* cited by examiner

Primary Examiner—D. Rutledge
(74) Attorney, Agent, or Firm—Fitzpatrick, Cella, Harper & Scinto

(57) ABSTRACT

An eye fundus camera includes mainly an illumination optical system, a photography optical system, a photography switch, a controller, and a display. The photography optical system includes a first filter and a second filter. The first filter exhibits a spectral characteristic of intercepting light of wavelengths falling within the first wavelength band and transmitting light of wavelengths falling within a second wavelength band of longer wavelengths than the first wavelength band. The second filter exhibits a spectral characteristic of transmitting light of wavelengths falling within a wavelength band which covers the second wavelength band and includes part of the first wavelength band and which is therefore wider than the second wavelength band including the wavelengths of the light transmitted by the first filter. At least the first filter can be inserted into an optical path and displaced therefrom.

38 Claims, 9 Drawing Sheets

EYE FUNDUS CAMERA

BACKGROUND OF THE INVENTION

1. Field of the Invention

The present invention relates to an eye fundus camera for photographing and recording an image of a subject's eye in a hospital of ophthalmology or the like. More particularly, this invention is concerned with an eye fundus camera suitable for fluorescence contrast photography.

2. Description of the Related Art

For performing fluorescence contrast photography using an eye fundus camera, a fluorescein that fluoresces in response to excitation light of specified wavelengths is intravenously injected into a patient. The fundus of the patient's eye is illuminated with the excitation light, and the fluorescent fundus is photographed. Indocyanine green or the like is employed as the fluorescein in infrared fluorescence photography in which infrared light that is invisible light is adopted as the excitation light.

FIG. 9 shows a typical configuration of a conventional eye fundus camera capable of performing infrared fluorescence photography. Since infrared light is utilized, an infrared television camera is used for observation or recording. A patient lying near a base 1 wears a face holder 2. A fixation lamp 3 is mounted on the face holder 2. A stage 4 whose position is adjustable back and forth, right and left, and up and down is placed on the top of the base 1. A housing 6 for accommodating an optical system composed of optical elements including an exciter filter 5 for infrared fluorescence designed for eye fundus cameras, and an operator stick having a position adjustment lever 7 and a photography switch 8 are mounted on the stage 4. A 35-mm film camera 9, an optical finder 10, and a relay lens unit 12 are fixed to the housing 6. The 35-mm film camera 9 is employed in color photography or visible-light fluorescence photography. An operator observes a fundus with the naked eyes through the optical finder 10. The relay lens unit 12 includes a barrier filter 11 used for infrared-fluorescence recording and enables mounting of a television camera. An infrared television camera 15 used for observation can be mounted on the optical finder 10 via a relay lens unit 14 that enables mounting of a television camera and includes a barrier filter 13 used for infrared-fluorescence observation. An output of the television camera 15 is fed to an observation display 16 over a cable. On the other hand, an infrared television camera 17 used for recording is mounted on the relay lens unit 12. An output of the television camera 17 is fed to an image recording device 18 and a display 19 used to display a record image over a cable.

The foregoing conventional eye fundus camera has an optical path defined independently for observation and recording alike. Therefore, the relay lens unit 14 for observation, infrared television camera 15 for observation, and display 16 for displaying a view image must be arranged along an optical path different from an optical path along which the relay lens unit 12 for recording, infrared television camera 17 for recording, and display 19 for displaying a record image are arranged. This leads to a complex structure and a large number of parts, and poses a problem in that the eye fundus camera becomes large in size and expensive.

Moreover, the infrared television camera 15 is connected to the optical finder 10 via the relay lens unit 14 in order to produce a view image seen through the optical finder 10. When an operator sees through the optical finder 10 for color photography or visible-light fluorescent photography, the operator must dismount the relay lens unit 14. Moreover, the cable extending from the infrared television camera 15 mounted on the relay lend unit 14 can get entangled and thus interfere with the manipulation of the eye fundus camera. These factors pose a problem in that they hinder improvement in maneuverability of the eye fundus camera.

SUMMARY OF THE INVENTION

Accordingly, an object of the present invention is to solve the foregoing problems and to provide an eye fundus camera that is compact and low-cost and offers excellent maneuverability. According to one aspect, the present invention that achieves at least one of these objectives relates to an eye fundus camera comprising an illumination optical system configured to illuminate the fundus of a patient's eye with light of wavelengths falling within a first wavelength band, and a photography optical system configured and positioned to form an image of the fundus illuminated by the illumination optical system so that a fundus image will be produced by the camera. The photography optical system includes a first filter that exhibits a spectral characteristic of intercepting light of wavelengths falling within the first wavelength band and transmitting light of wavelengths falling within a second wavelength band of longer wavelengths than the first wavelength band, and a second filter that exhibits a spectral characteristic of transmitting light of wavelengths falling within a wavelength band that covers the second wavelength band and includes part of the first wavelength band and that is therefore wider than the second wavelength band including the wavelengths of the light transmitted by the first filter. At least the first filter is capable of being inserted into an optical path of the photography optical system and displaced therefrom. The camera also comprises a photography switch with which an operator gives instructions to photograph the fundus image as still images under strobe light, a controller for causing a strobe to produce the strobe light when the photography switch is pressed and the first filter is inserted into the optical path, and a display for displaying the fundus image produced by the photography optical system.

The illumination optical system includes an exciter filter that exhibits a spectral characteristic of transmitting light of wavelengths falling within the first wavelength band and intercepting light of wavelengths falling within the second wavelength band, and that is displaceable from the optical path. In addition, for enabling observation, the controller causes the first filter to be displaced from the optical path and causes the second filter to be inserted thereinto, and for enabling photography, the controller causes the first filter to be inserted into the optical path. Also, the photography switch can comprise a double switch, and in this case, the controller controls insertion of the second filter in response to pressing of a first-step switch of the double switch, and controls flashing of the strobe light in response to pressing of a second-step switch thereof. Further, when the time interval between the pressing of the first-step switch and the pressing of the second-step switch is smaller than a predetermined value, the controller disables insertion of the second filter. Moreover, in one embodiment, the eye fundus camera enables fluorescence photography of an eye fundus with fluorescein, the first wavelength band includes wavelengths suitable for excitation of the fluorescein, and the second wavelength band includes wavelengths of light produced by fluorescence of the excited fluorescein.

According to another aspect, the present invention that achieves at least one of these objectives relates to an eye fundus camera comprising an illumination optical system for illuminating a fundus of a patient's eye. The illumination optical system includes a first filter that exhibits a spectral characteristic of transmitting light of wavelengths falling within a first wavelength band and intercepting light of wavelengths falling within a second wavelength band of longer wavelengths than the first wavelength band, and a second filter that exhibits a spectral characteristic of transmitting light of wavelengths falling within a wavelength band which covers the first wavelength band and includes part of the second wavelength band and that is therefore wider than the first wavelength band including the wavelengths of the light transmitted by the first filter. At least the first filter is capable of being inserted into an optical path of the illumination optical system and displaced therefrom. The camera also comprises a photography optical system for forming an image of a fundus illuminated by the illumination optical system so that the fundus image will be produced by the photography optical system. The photography optical system including a third filter that exhibits a spectral characteristic of intercepting light of wavelengths falling within the first wavelength band and transmitting light of wavelengths falling within the second wavelength band. The camera also comprises a display for displaying the fundus image produced by the photography optical system.

The camera can also comprise a controller for enabling observation by causing the first filter to be displaced from the optical path and causing the second filter to be inserted into the optical path, and for enabling photography by causing the first filter to be inserted into the optical path. In addition, the camera can also comprise a photography switch with which an operator instructs the camera to photograph the fundus image as still images under strobe light, and a controller for, when the photography switch is pressed, causing a strobe to produce the strobe light with the first filter inserted into the optical path. The photography switch can comprise a double switch, and in this case, the controller causes the second filter to be inserted into the optical path in response to pressing of a first-step switch of the double switch, and causes the strobe to produce the strobe light in response to pressing of a second-step switch thereof. In one embodiment, the eye fundus camera enables fluorescence photography of a fundus with fluorescein, the first wavelength band includes wavelengths suitable for excitation of the fluorescein, and the second wavelength band includes wavelengths of light produced by the fluorescence of the excited fluorescein.

According to yet another aspect, the present invention that achieves at least one of these objective relates to an eye fundus infrared camera suitable for infrared fluorescence photography comprising an illumination optical system for illuminating a fundus of a patient's eye with excitation light of wavelengths suitable to fluoresce fluorescein and a photography optical system for forming an image of the eye fundus illuminated by the illumination optical system so that a fundus image will be produced by the infrared camera. The photography optical system includes a first barrier filter that exhibits a spectral characteristic of intercepting the excitation light and transmitting light of wavelengths that are longer than the wavelengths of the excitation light produced by the fluorescence of fluorescein, and a second barrier filter that exhibits a spectral characteristic of transmitting light of wavelengths falling within a wavelength band which covers the wavelengths of the light produced by the fluorescence of fluorescein and includes part of the wavelengths of the excitation light and which is therefore wider than the wavelength band including the wavelengths of the light produced by the fluorescence of fluorescein and being transmitted by the first barrier filter. At least the first barrier filter is capable of being inserted into the optical path of the photography optical system and displaced therefrom. The camera further comprises a photography switch with which an operator instructs the infrared camera to photograph the fundus image as still images under strobe light and a controller for causing, when the photography switch is pressed, a strobe to produce the strobe light with the first barrier filter inserted into the optical path. In addition, the camera comprises a display for displaying the fluorescence fundus image produced by the infrared camera.

According to yet another aspect, the present invention that achieves at least one of these objectives relates to an eye fundus infrared camera suitable for fluorescence photography comprising an illumination optical system for illuminating a fundus of a patient's eye with excitation light of wavelengths suitable to fluoresce fluorescein. The illumination optical system includes a first exciter filter that exhibits a spectral characteristic of transmitting light of wavelengths falling within a first wavelength band and intercepting light of wavelengths that are longer than the wavelengths of the first wavelength band produced by the fluorescence of fluorescein, and a second exciter filter that exhibits a spectral characteristic of transmitting light of wavelengths falling within a wavelength band which covers the wavelengths of the excitation light and includes part of the wavelengths of the light produced by the fluorescence of fluorescein and which is therefore wider than the first wavelength band including the wavelengths of the light transmitted by the first exciter filter. At least the first exciter filter is capable of being inserted into an optical path of the illumination optical system and displaced therefrom. The camera further comprises a photography optical system for forming an image of the fundus illuminated by the illumination optical system so that the fundus image will be produced by the infrared camera. The photography optical system includes a barrier filter that exhibits a spectral characteristic of intercepting the excitation light and transmitting the light produced by the fluorescence of fluorescein, and a display for displaying the fluorescence fundus image produced by the photography optical system. In one embodiment, the fluorescein is indocyanine green.

According to still another aspect, the present invention that achieves at least one of these objectives relates to a method of performing fluorescence photography of an eye fundus with an eye fundus camera comprising the steps of illuminating the fundus of a patient's eye with light of wavelengths only falling within a first wavelength band, transmitting light reflected by the fundus only in a portion of the first wavelength band through a photography optical system to an infrared television camera to produce a fundus image, displaying the fundus image to permit an operator of the fundus camera to align and focus the fundus camera while viewing the displayed fundus image, measuring the time from injection of a fluorescein into the patient's eye, the fluorescein fluorescing and producing light of wavelengths falling into a second wavelength band in response to being exposed to excitation light in the first wavelength band, transmitting light only in the second wavelength band from the patient's eye produced by the fluorescing of the fluorescein through the photography optical system to the infrared television camera, and recording a motion picture of the fundus and displaying the fundus image produced by the infrared camera using the light only in the second wavelength band from the patient's sys produced by the fluorescing of the fluorescein.

The illuminating step can comprise the step of inserting an exciter filter transmitting light of wavelengths only falling within a first wavelength band into the optical path of an illumination optical system. The first transmitting step can comprise the step of inserting a first barrier filter transmitting light only in the portion of the first wavelength band into the optical path of the photography optical system. The measuring step can be performed by starting a timer. The second transmitting step can comprise the step of removing the first barrier filter from the optical path of the photography optical system and inserting a second barrier filter transmitting light of wavelengths only in the second wavelength band into the optical path of the photography optical system.

In addition, the method can further comprise the steps of transmitting light reflected by the fundus only in the portion of the first wavelength band through a photography optical system to the infrared television camera to produce a fundus image using the first-wavelength-band light in response to the elapsing of a predetermined time from the time of injection of a fluorescein into the patient's eye measured in the measuring step, displaying the fundus image produced using the first-wavelength-band light to permit an operator of the fundus camera to designate a region of the fundus to be photographed, transmitting light only in the second wavelength band from the patient's eye produced by the fluorescing of the fluorescein through the photography optical system to the infrared television camera in response to a photography switch being pressed by the operator, stopping the illuminating step, flashing strobe light to illuminate the patient's eye with strobe light, and recording still images of the strobe-illuminated fundus of the patient's eye in response to a photography switch being pressed by the operator, stopping the measuring operation performed in the measuring step, and terminating the recording of still images in response to the stopping of the measuring operation in the measuring-operation stopping step.

Further, the transmitting step performed in response to the elapsing of the predetermined time is performed by displacing the second barrier filter out of the optical path of the photography optical system and inserting the first barrier filter into the optical path of the photography optical system. In addition, the transmitting step of transmitting light only in the second wavelength band in response to a photography switch being pressed by the operator is performed by displacing the first barrier filter out of the optical path of the photography optical system and inserting the second barrier filter into the optical path of the photography optical system.

In addition, the method can further comprise the steps of stopping the illuminating step, flashing strobe light to illuminate the patient's eye with strobe light, and recording still images of the strobe-illuminated fundus of the patient's eye in response to both a determination that a predetermined amount of time has not elapsed from the time of injection of a fluorescein into the patient's eye measured in the measuring step and a photography switch being pressed by the operator.

According to still another aspect, the present invention that achieves at least one of these objectives relates to a method of performing fluorescence photography of an eye fundus with an eye fundus camera comprising the steps of illuminating the fundus of a patient's eye with light of wavelengths only falling within a first wavelength band and a portion of a second wavelength band of longer wavelengths than the first wavelength band, transmitting light reflected by the fundus only in the portion of the second wavelength band from a photography optical system to an infrared television camera to produce a fundus image, displaying the fundus image to permit an operator of the fundus camera to align and focus the fundus camera while viewing the displayed fundus image, measuring the time from injection of a fluorescein into the patient's eye, the fluorescein fluorescing and producing light of wavelengths falling into the second wavelength band in response to being exposed to excitation light in the first wavelength band, transmitting light only in the second wavelength band from the patient's eye produced by the fluorescing of the fluorescein from the photography optical system to the infrared television camera, and recording a motion picture of the fundus and displaying the fundus image produced by the infrared camera using the light only in the second wavelength band from the patient's eye produced by the fluorescing of the fluorescein.

The illuminating step comprises the step of inserting a first exciter filter transmitting light of wavelengths only falling within a first wavelength band and the portion of the second wavelength band into the optical path of an illumination optical system. The first transmitting step comprises the step of inserting a barrier filter transmitting light only in the second wavelength band into the optical path of the photography optical system. The measuring step is performed by starting a timer. The second transmitting step comprises the step of removing the first exciter filter from the optical path of the illumination optical system and inserting a second exciter filter transmitting light of wavelengths only in the first wavelength band into the optical path of the illumination optical system.

The method can further comprise the steps of transmitting light reflected by the fundus only in the portion of the second wavelength band from the photography optical system to the infrared television camera to produce a fundus image by using the light illuminating the fundus from the illumination optical system in response to the elapsing of a predetermined time from the time of injection of a fluorescein into the patient's eye measured in the measuring step, displaying the fundus image produced by using the light illuminating the fundus from the illumination optical system to permit an operator of the fundus camera to designate a region of the fundus to be photographed, transmitting light only in the second wavelength band from the patient's eye produced by the fluorescing of the fluorescein from the photography optical system to the infrared television camera in response to a photography switch being pressed by the operator, stopping the illuminating step, flashing strobe light to illuminate the patient's eye with strobe light, and recording still images of the strobe-illuminated fundus of the patient's eye in response to a photography switch being pressed by the operator, stopping the measuring operation performed in the measuring step and terminating the recording of still images in response to the stopping of the measuring operation in the measuring-operation stopping step.

The transmitting step performed in response to the elapsing of the predetermined time is performed by displacing the second exciter filter out of the optical path of the illumination optical system. The transmitting step of transmitting light only in the second wavelength band in response to a photography switch being pressed by the operator is performed by displacing the first exciter filter out of the optical path of the illumination optical system and inserting the second exciter filter into the optical path of the illumination optical system.

In addition, the method can further comprise the steps of stopping the illuminating step, flashing strobe light to illuminate the patient's eye with strobe light, and recording still images of the strobe-illuminated fundus of the patient's eye in response to both a determination that a predetermined amount of time has not elapsed from the time of injection of a fluorescein into the patient's eye measured in the measuring step and a photography switch being pressed by the operator.

According to still another aspect, the present invention that achieves at least one of these objectives relates to an eye fundus camera comprising means for illuminating the fundus of a patient's eye with light of wavelengths falling within a first wavelength band, means for forming an image of the fundus illuminated by the illuminating means and for photographing the image. The image forming means includes first filter means for intercepting light of wavelengths falling within the first wavelength band and transmitting light of wavelengths falling within a second wavelength band of longer wavelengths than the first wavelength band, and second filter means for transmitting light of wavelengths falling within a wavelength band that covers the second wavelength band and includes part of the first wavelength band and that is therefore wider than the second wavelength band including the wavelengths of the light transmitted by the first filter means. At least the first filter means is capable of being inserted into an optical path of the image forming means and displaced therefrom. The camera also comprises operator-actuated means for instructing the photographing of the fundus image with the image forming means as still images under strobe light, control means for controlling a strobe to produce the strobe light when the operator-actuated means is actuated and the first filter means is inserted into the optical path, and display means for displaying the fundus image produced by he image forming means.

The illuminating means includes exciter filter means for transmitting light of wavelengths falling within the first wavelength band and intercepting light of wavelengths falling within the second wavelength band, and that is displaceable from the optical path. For enabling observation, the control means controls the first filter means to be displaced from the optical path and controls the second filter means to be inserted thereinto. For enabling photography, the control means controls the first filter means to be inserted into the optical path. The operator-actuated means can comprise double instruction means for permitting the operator to input two different instructions into the camera. In this embodiment, the control means controls insertion of the second filter means in response to the operator actuating first instruction means of the double instruction means, and the control means controls flashing of the strobe light in response to the operator actuating second instruction means of the double insertion means. When the time interval between the actuating the first instruction means and actuating the second instruction means is smaller than a predetermined value, the control means disables insertion of the second filter means. In addition, in one embodiment, the eye fundus camera enables fluorescence photography of an eye fundus with fluorescein, the first wavelength band includes wavelengths suitable for excitation of the fluorescein, and the second wavelength band includes wavelengths of light produced by fluorescence of the excited fluorescein.

According to still another aspect, the present invention that achieves at least one of these objectives relates to an eye fundus camera comprising illuminating means for illuminating a fundus of a patient's eye. The illuminating means includes first filter means for transmitting light of wavelengths falling within a first wavelength band and intercepting light of wavelengths falling within a second wavelength band of longer wavelengths than the first wavelength band, and second filter means for transmitting light of wavelengths falling within a wavelength band that covers the first wavelength band and includes part of the second wavelength band and that is therefore wider than the first wavelength band including the wavelengths of the light transmitted by the first filter means. At least the first filter means is capable of being inserted into an optical path of the illuminating means and displaced therefrom. The camera also comprises means for forming an image of a fundus illuminated by the illuminating means and photographing the fundus image. The image forming means includes third filter means for intercepting light of wavelengths falling within the first wavelength band and transmitting light of wavelengths falling within the second wavelength band, and display means for displaying the fundus image produced by the image forming means.

The camera can further comprise control means for enabling observation by controlling the first filter means to be displaced from the optical path and controlling the second filter means to be inserted into the optical path, and for enabling photography by controlling the first filter means to be inserted into the optical path. In addition, the camera can further comprise operator-actuated means for instructing the camera to photograph the fundus image as still images under strobe light, and control means for, when the operator-actuated means is actuated by the operator, controlling a strobe to produce the strobe light with the first filter means inserted into the optical path. The operator-actuated means comprises double instruction means for permitting the operator to input two different instructions into the camera. In this embodiment, the control means controls the second filter means to be inserted into the optical path in response to the operator actuating first instruction means of the double instruction means, and controls the strobe to produce the strobe light in response to the operator actuating second instruction means of the double instruction means. In addition, the eye fundus camera enables fluorescence photography of a fundus with fluorescein, the first wavelength band includes wavelengths suitable for excitation of the fluorescein, and the second wavelength band includes wavelengths of light produced by the fluorescence of the excited fluorescein.

According to yet another aspect, the present invention that achieves at least one of these objectives relates to an eye fundus infrared camera suitable for infrared fluorescence photography comprising illuminating means for illuminating a fundus of a patient's eye with excitation light of wavelengths suitable to fluoresce fluorescein, and means for forming an image of the eye fundus illuminated by the illuminating means and photographing the fundus image. The image forming means includes first barrier filter means for intercepting the excitation light and transmitting light of wavelengths that are longer than the wavelengths of the excitation light produced by the fluorescence of fluorescein, and second barrier filter means for transmitting light of wavelengths falling within a wavelength band which covers the wavelengths of the light produced by the fluorescence of fluorescein and includes part of the wavelengths of the excitation light and which is therefore wider than the wavelength band including the wavelengths of the light produced by the fluorescence of fluorescein and being transmitted by the first barrier filter means. At least the first barrier filter means is capable of being inserted into the optical path of the photography optical system and displaced therefrom. The camera also includes operator-actuated means for instructing the photographing of the fundus image with the image forming means as still images under strobe light, control means for causing, when the operator-actuated means is actuated, a strobe to produce the strobe light with the first barrier filter means inserted into the optical path, and display means for displaying the fluorescence fundus image produced by the infrared camera.

According to still another aspect, the present invention that achieved at least one of these objectives relates to an eye fundus infrared camera suitable for fluorescence photography comprising illuminating means for illuminating a fundus of a patient's eye with-excitation light of wavelengths suitable to fluoresce fluorescein. The illuminating means includes first exciter filter means for transmitting light of wavelengths falling within a first wavelength band and intercepting light of wavelengths that are longer than the wavelengths of the first wavelength band produced by the fluorescence of fluorescein, and second exciter filter means for transmitting light of wavelengths falling within a wavelength band that covers the wavelengths of the excitation light and includes part of the wavelengths of the light produced by the fluorescence of fluorescein and that is therefore wider than the first wavelength band including the wavelengths of the light transmitted by the first exciter filter means. At least the first exciter filter means is capable of being inserted into an optical path of the illuminating means and displaced therefrom. The camera also comprises means for forming an image of the fundus illuminated by the illuminating means and photographing the fundus image. The image forming means includes barrier filter means for intercepting the excitation light and transmitting the light produced by the fluorescence of fluorescein, and display means for displaying the fluorescence fundus image produced by the image forming means. In one embodiment, the fluorescein is indocyanine green.

Further objects, features and advantages of the present invention will become apparent from the following description of the preferred embodiments with reference to the attached drawings.

DESCRIPTION OF THE PREFERRED EMBODIMENTS

Figure 1:
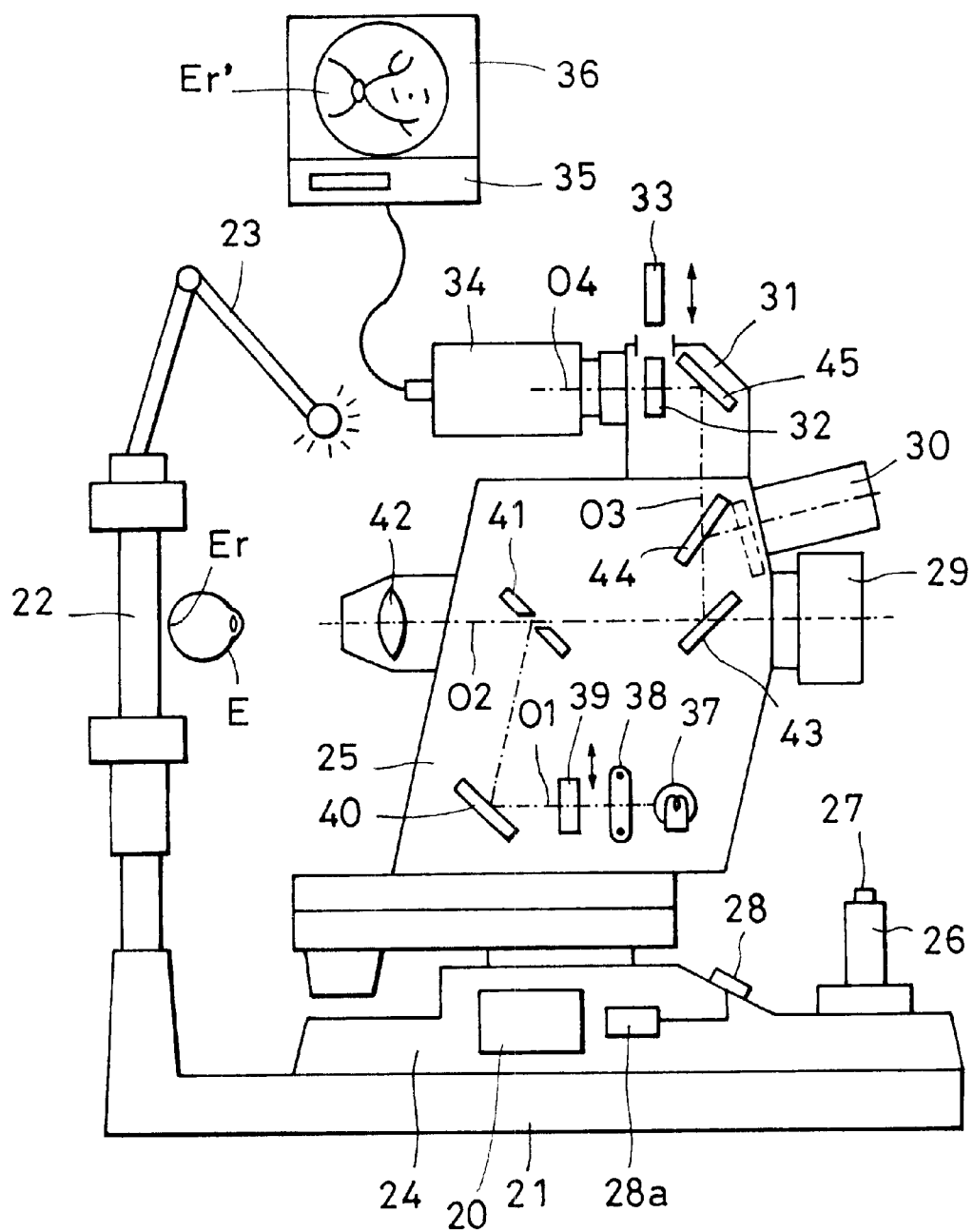
FIG. 1 shows the configuration of an eye fundus camera in accordance with the first embodiment of the present invention.

FIG. 1 shows the configuration of an eye fundus camera capable of operating in an infrared fluorescence photography mode in addition to an ordinary photography mode. A face holder 22 is located on a margin of a base 21 near which a patient lies. A fixation lamp 23 is mounted on the top of the face holder 22. A stage 24 whose position is adjustable back and forth, right and left, and up and down is placed on the top of the base 21. An optical unit 25 designed for eye fundus cameras, an operator stick having a position adjustment lever 26 and an photography switch 27, and a timer switch 28 are mounted on the stage 24. The timer switch 28 is used to activate a timer 28a for indicating a time that has elapsed since completion of the intravenous injection of a fluorescein. A controller 20 controlling the whole eye fundus camera and including a computer is incorporated in the stage 24.

A 35-mm film camera 29 used for color photography or visible-light fluorescence photography, an optical finder 30 through which an operator observes a fundus with the naked eyes, and a relay lens unit 31 enabling mounting of a television camera, are mounted on the periphery of the optical unit 25. A barrier filter 32 used for infrared fluorescence recording and a barrier filter 33 used for infrared fluorescence observation are selectively inserted into an optical path O4 in the relay lens unit 31 under the control of the controller 20. An infrared television camera 34 is mounted on the relay lens unit 31. When infrared fluorescence photography is not carried out, an ordinary television camera is mounted on the relay lens unit. An output of the infrared television camera 34 is fed to an image recording device 35 having a disk and a memory on and in which a motion picture or still images can be recorded, and a display 36 for displaying a record image of a fundus.

A halogen lamp 37, a strobe 38, an exciter filter 39 used for infrared fluorescence, a mirror 40, and a perforated mirror 41, which together constitute an illumination optical system are arranged in that order along an optical path O1 in the optical unit 25. A mechanism for inserting the exciter filter 39 into the optical path O1 or displacing it from the optical path under the control of the controller 20 is included to enable an operator to select either insertion of the exciter filter 39 or displacement thereof. An objective 42, a perforated mirror 41, and a light splitting element 43 are arranged along an optical path O2 that leads to the 35-mm film camera 29. A switching mirror 44 and a mirror 45 are arranged along an optical path O3 extending in a direction in which the light splitting element 43 reflects light. A barrier filter 32 that is a first filter (or a barrier filter 33 that is a second filter) and the infrared television camera 34 are arranged along the optical path O4 extending in a direction in which the mirror 45 reflects light. One of the barrier filters 32 and 33 is inserted into the optical path by a filter drive unit (not shown), and the other barrier filter is displaced from the optical path. The optical finder 30 is located in a direction in which the switching mirror 44 reflects light. The groups of optical elements arranged along the optical paths O2, O3, and O4 respectively constitute a photography optical system enabling both observation and photography of a patient's eye.

Figure 4:
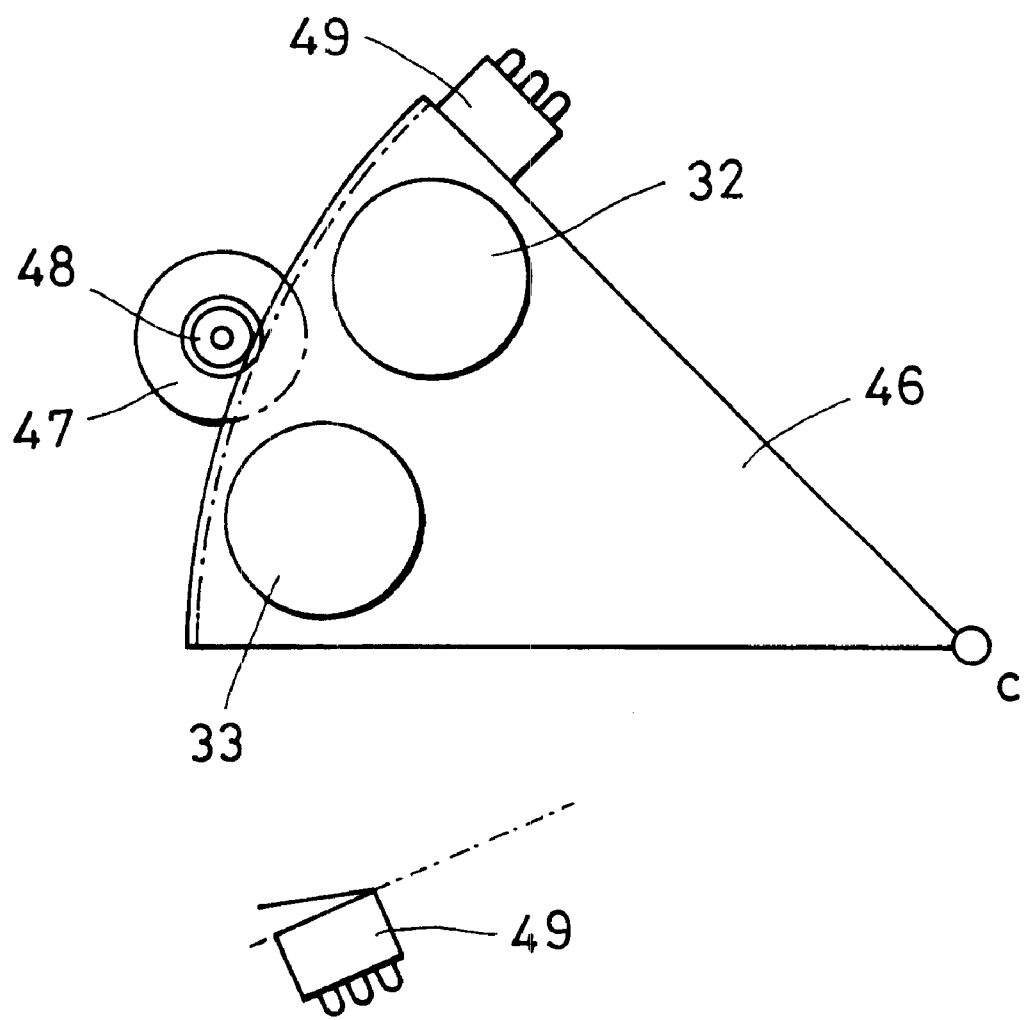
FIG. 4 shows the structure of a filter driving means.

FIG. 4 shows a practical structure of a filter drive unit. A sector plate 46 having a gear formed as an arc portion thereof can rotate around an axis of rotation C as a center. The barrier filter 32 and barrier filter 33 are attached to the sector plate 46. A pinion 48 attached to a driving motor 47 is meshed with the gear of the sector plate 46. Two microswitches 49 are located on both sides of the sector plate 46 and used to position the barrier filters 32 and 33. Owing to this mechanism, the direction of rotation of the driving motor 47 can be reversed in order to switch the barrier filters 32 and 33.

Figure 2:
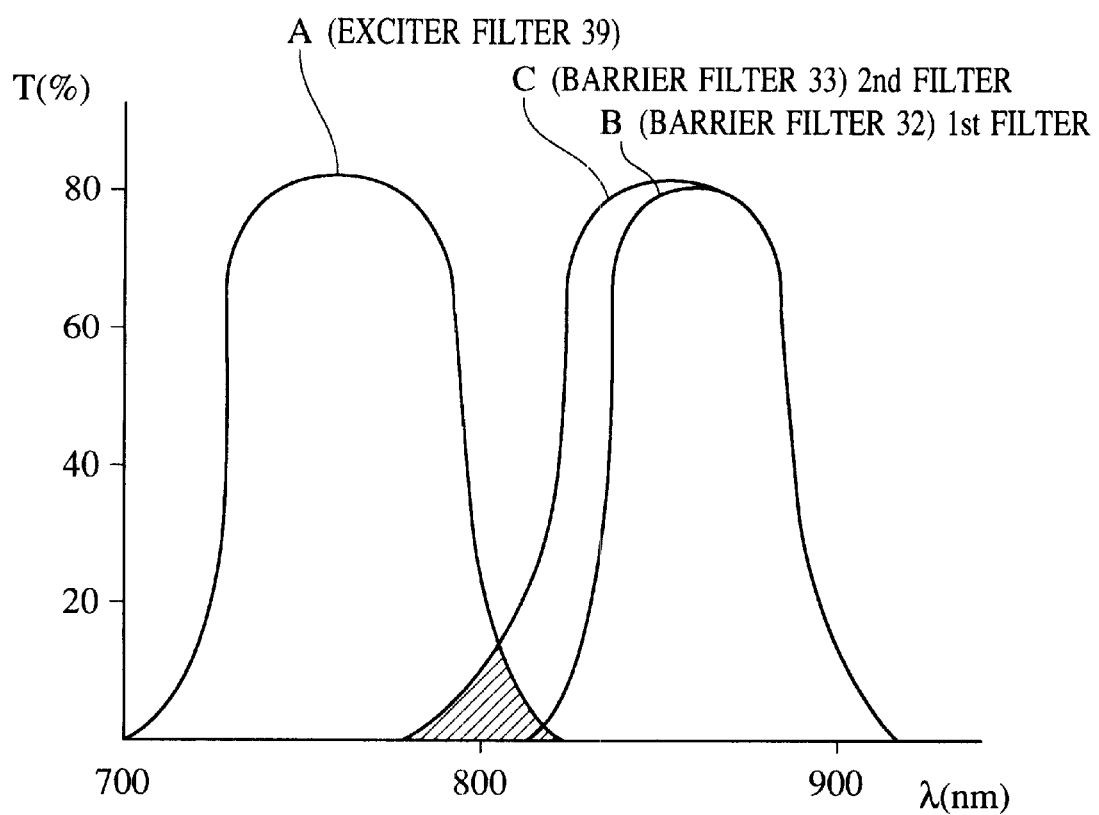
FIG. 2 is a graph indicating the characteristics of filters employed in the first embodiment.

Indocyanine green or the like is employed as a fluorescein in infrared fluorescence photography in which infrared light whose wavelengths are selected by the exciter filter 39 included in the illumination optical system is used as excitation light. FIG. 2 is a graph indicating the transmission characteristics of the exciter filter 39 for infrared fluorescence, barrier filter 32, and barrier filter 33 in the form of characteristic curves A, B, and C. The ordinate axis indicates the transmittance T (%) and the abscissa axis indicates the wavelength λ (nm). The exciter filter 39 is designed in line with the characteristic of indocyanine green. The exciter filter 39 exhibits a characteristic like the wavelength-versus-transmission characteristic A of selectively transmitting infrared light of wavelengths falling within a first wavelength band (mainly 720 nm to 800 nm). The barrier filter 32 exhibits wavelength-versus-transmission characteristic B. Specifically, the barrier filter 32 transmits light, which stems from fluorescence of excited indocyanine green and whose wavelengths fall within a second wavelength band (mainly 810 nm to 900 nm), and intercepts excitation light (first wavelength band). The barrier filter 33 exhibits the wavelength-versus-transmission characteristic C of transmitting light of wavelengths (mainly 790 nm to 900 nm) falling within a wavelength band covering the second wavelength band and including part of the long wavelengths of excitation light (wavelengths falling within a hatched range in FIG. 2).

When the exciter filter 39 (characteristic A) and barrier filter 32 (characteristic B) are used in combination, the characteristic curves A and B do not substantially overlap to share the same wavelength band. Therefore, a fundus image Er' of a patient's eye E cannot be produced on the display 36 until light is produced by fluorescence after intravenous injection. An operator cannot help waiting for light stemming from fluorescence and then starting preparations for photography, such as alignment and focusing. It is impossible to photograph the image Er' immediately after light is produced by fluorescence. Moreover, when a long time has elapsed since intravenous injection, light produced by fluorescence gets feeble. Consequently, the image Er' formed by illuminating a fundus with the halogen lamp 37 becomes indistinct and hard to see. This brings about an obstacle to preparations for photography. For overcoming this drawback, according to the present embodiment, the barrier filter 33 (characteristic C) is used. This is because the barrier filter 33 exhibits the characteristic of transmitting part of light reflected from a fundus Er illuminated with excitation light, that is, light of wavelengths falling within the hatched range in FIG. 2. The transmittance exhibited by the barrier filter 33 relative to the light of wavelengths falling within the hatched range in FIG. 2 is not very high (20% or less). Even in an early stage of photography in which fluorescence has not yet occurred or in a late stage thereof in which fluorescence fades away, it is possible to perform photography using the infrared television camera 34. An operator can view the fundus image Er'.

For infrared fluorescence contrast photography, a fluorescein is intravenously injected into a patient. A time-passing change in intensity of fluorescence occurring after injection is maximized in the early stage immediately after the intravenous injection in which the most intense fluorescence occurs. Fluorescence fades away with the passage of time. Since the intense fluorescence occurs in the early stage after the intravenous injection, images formed under light emanating from the strobe 38 can be recorded as still images. Besides, images formed under light emanating from the halogen lamp 37 can be recorded as a motion picture. Thereafter, when the fluorescence fades away, the amount of light emanating from the halogen lamp 37 is too small to record images as a motion picture. Only the images formed under light emanating from the strobe 38 can be recorded as still images.

Figure 3:
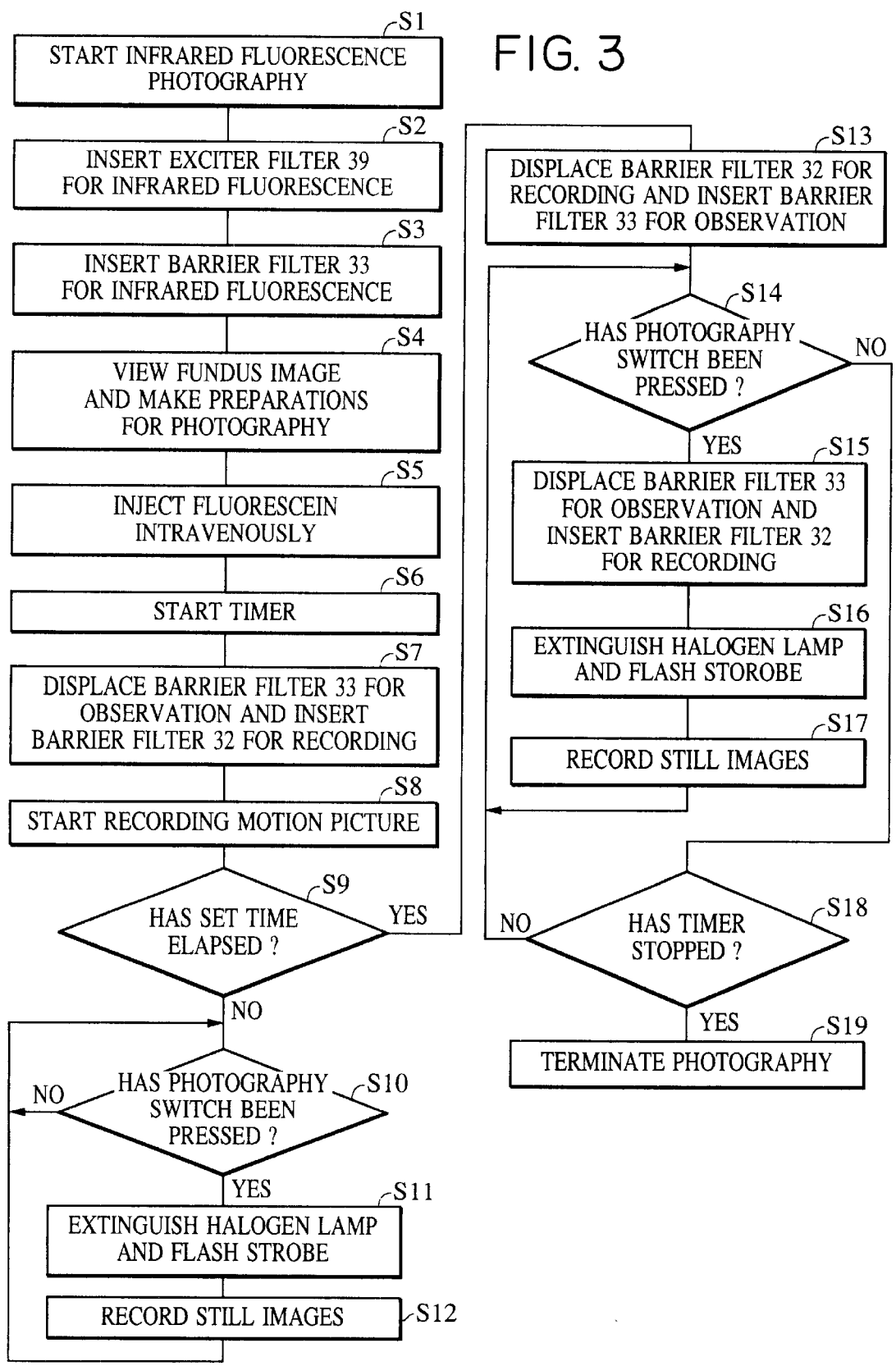
FIG. 3 is a flowchart.

FIG. 3 is a flowchart describing a photography procedure. For ordinary photography, the exciter filter 39 is displaced from and out of the optical path O1. For infrared fluorescence photography, which is started in step S1, the exciter filter 39 is inserted into the optical path O1 in step S2. A patient is asked to take a seat. The patient' face is locked in the face holder 22 so that the patient's eye E will be opposed to the objective 42. An operator moves the stage 24 using the position adjustment lever 26 so as to align the optical path O2 substantially with the patient's eye E. The exciter filter 39 is then inserted into the optical axis O1. The switching mirror 44 is displaced from and out of the optical path O3 and located at a position indicated with a dashed line in FIG. 1. The barrier filter 33 is inserted into the optical path O4 in place of the barrier filter 32 in step S3.

Light emanating from the halogen lamp 37 is passed through the exciter filter 39 and mirror 40 and reflected from the perforated mirror 41. The light then illuminates the fundus Er of the patient's eye E through the objective 42. The light reflected from the fundus is passed through the objective 42 and the hole of the perforated mirror 41, reflected from the light splitting element 43 and mirror 45, and reaches the infrared television camera 34. A fundus image Er' formed with light of wavelengths falling within the hatched range in FIG. 2 is displayed on the display 36 and viewed by the operator in step S4. The operator makes preparations for photography including alignment and focusing while looking at the display 36 also in step S4.

After the preparations are completed, a fluorescein is intravenously injected into the patient in step S5. The operator presses the timer switch 28 to start the timer 28a in step S6. Accordingly, in step S7, the controller 20 takes the barrier filter 33 out of the optical path O4 and insets the barrier filter 32 into the optical path O4. The image recording device 35 is used to start recording a motion picture and timer information (a time having elapsed since the start of the timer) in step S8. The fluorescein then flows into the ophthalmic blood vessels. The excitation light that illuminates the fundus E brings about fluorescence. Consequently, a fluorescence fundus image Er' is visualized on the display 36. The operator can now observe the fundus. The process is recorded in the form of a motion picture. If necessary, the operator finely adjust the focus of the infrared television camera, and adjust the amount of light emanating from the halogen lamp 37 according to a change in the intensity of fluorescence.

In step S9, the controller 20 determines whether the predetermined time set by the timer 28a has elapsed. If not, controller 20 determines whether the operator has pressed photography switch 27 in step S10. For photographing the fluorescence image as still images while photographing it as a motion picture, the operator presses the photography switch 27. When this occurs, under the control of the controller 20, while the barrier filter 32 remains inserted into the optical path O4, the halogen lamp 37 is extinguished and the strobe 38 is flashed in step S11. Consequently, still images of the fluorescence fundus image and timer information are recorded in the image recording device 35 in step S12.

When some time elapses after intravenous injection, fluorescence fades away. The fundus image Er' displayed on the display 36 becomes indistinct and indiscernible. A time instant at which fluorescence fades away can be roughly predicted. The timer 28a is used to monitor passage of this predetermined time at which fluorescence fades. When the controller 20 determines that the time has elapsed in step S9, the barrier filter 32 on the optical path O4 is automatically switched with the barrier filter 33 under the control of the controller 20 in step S13. The image recording device 35 then stops motion-picture recording. Because of the characteristic of the barrier filter 33, not only light stemming from fluorescence but also light of wavelengths falling within the hatched range in FIG. 2 reaches the infrared television camera 34. The fundus image Er' is therefore visualized distinctly on the display 36. The operator designates a desired region to be photographed while looking at the display 36, and presses the photography switch 27. When the controller 20 determines that this action has occurred in step S14 in response to a signal generated responsively to the operator's action, the controller 20 again switches the barrier filter 33 on the optical path O4 with the barrier filter 32 in step S15. The halogen lamp 37 is then extinguished and the strobe 38 is flashed in step S16. Still images of the fluorescence fundus image Er' and timer information are then recorded in the image recording device 35 in step S17. A switch dedicated to switching of filters may be included for selecting either the barrier filter 32 or 33 on behalf of the timer 28a and photography switch 27. The process then returns to step S14. If the photography switch 27 is not determined to be pressed by controller 20, the controller 20 determines in step S18 whether the timer 28a stops measuring the predetermined time. If the controller 20 determines that the timer 28a has not stopped, the process returns to step S14. If the controller 20 determines that the timer 28a has stopped, the process advances to step S19 and controller 20 terminates photography.

For recording a fluorescence image, the barrier filter 33 need not always be displaced from the optical path. This is because even when the barrier filter 33 (characteristic C) and barrier filter 32 (characteristic B) are inserted in layers into the optical path, light of wavelengths falling within the hatched range in FIG. 2 and being used for observation is intercepted due to a combination of their characteristics. Consequently, the fluorescence image can be recorded successfully.

Figure 5:
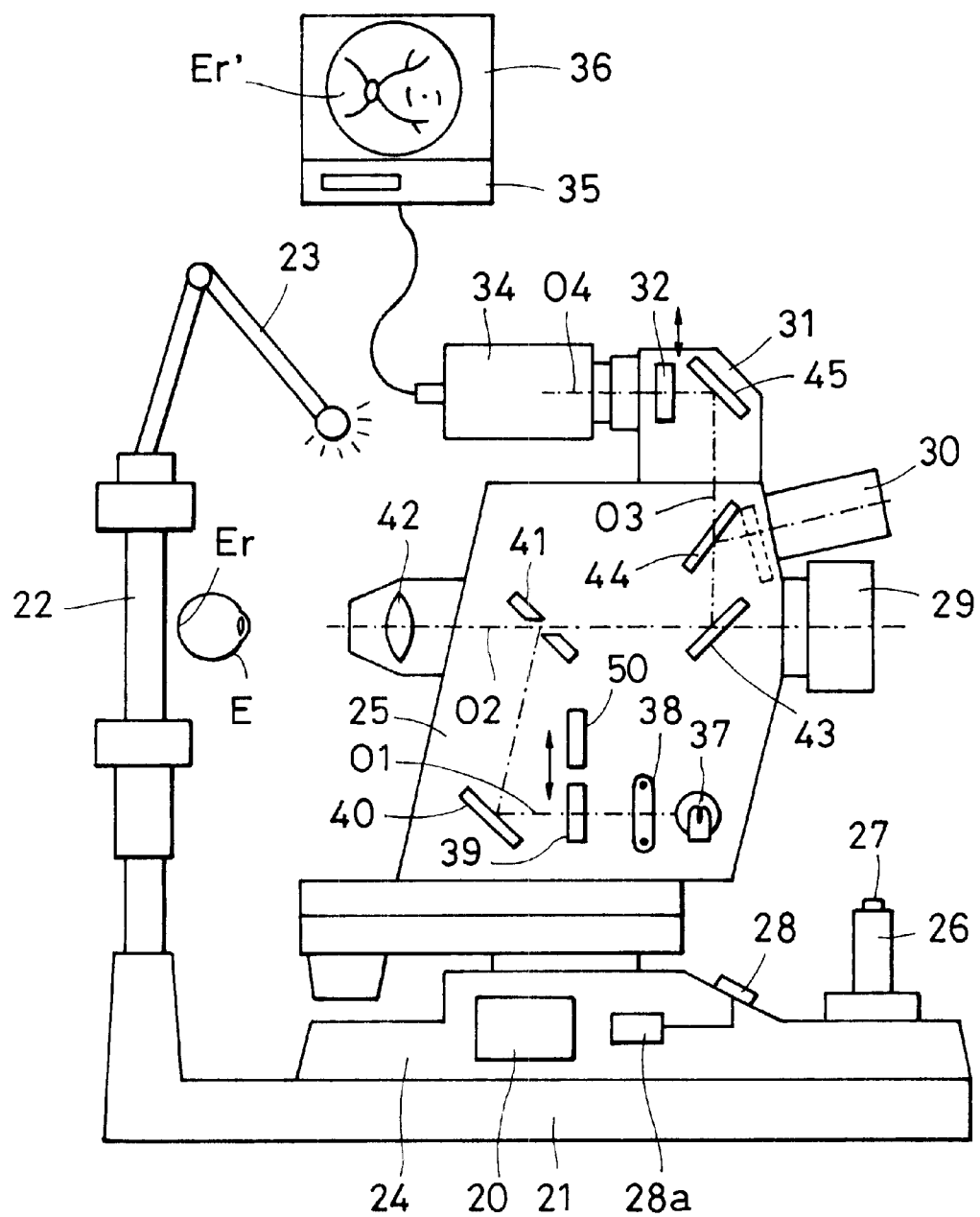
FIG. 5 shows the configuration of an eye fundus camera in accordance with the second embodiment.

FIG. 5 shows the configuration of an eye fundus camera in accordance with another embodiment. This embodiment is the same as the FIG. 1 embodiment, except as noted below. As a result, the same reference numerals denote the same elements in FIGS. 1 and 5. According to the previous embodiment, the barrier filter 32 for observation and the barrier filter 33 for recording are switched on the optical path in the photography optical system. In contrast, according to the present embodiment, either of two filters having different characteristics (exciter filter 39 and exciter filter 50) is selected and inserted into the optical path in the illumination optical system. A driving mechanism for switching the two filters may be identical to the one shown in FIG. 4. When the filters included in the photography optical system are switched as they are in the previous embodiment shown in FIG. 1, the focus of the infrared television camera varies with insertion of a filter in the photography optical system. In contrast, according to the present embodiment, since the filters included in the illumination optical system are switched, the variation of the focus does not occur. As a result, an image can be photographed more successfully.

Figure 6:
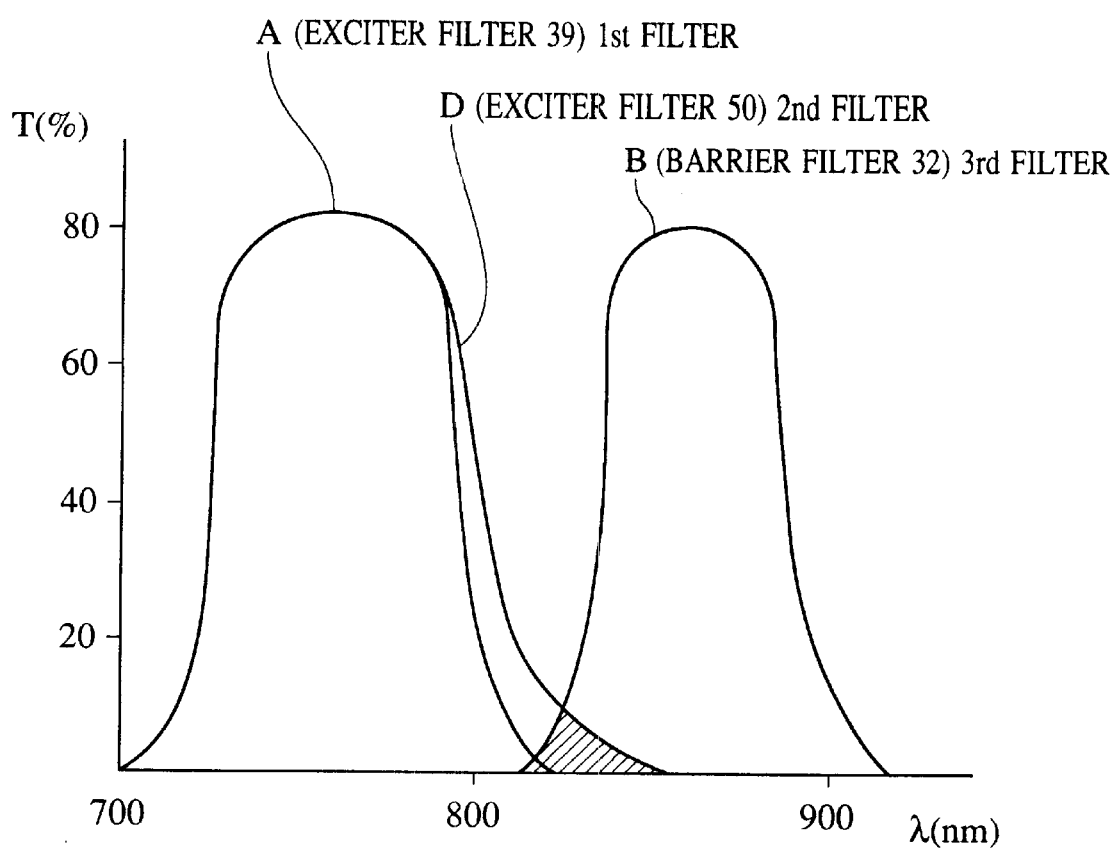
FIG. 6 is a graph indicating the characteristics of filters employed in the second embodiment.

The exciter filter 50 (second filter) for infrared fluorescence observation employed in the present embodiment exhibits a wavelength-versus-transmittance characteristic D shown in FIG. 6. The exciter filter 50 and the exciter filter 39 (first filter) for infrared fluorescence recording are switched under the control of the controller 20, whereby a fundus is photographed. The exciter filter 50 has the characteristic of selectively transmitting light of wavelengths falling within a wavelength band (mainly 700 mm to 820 nm) covering a first wavelength band and including part of a second wavelength band (long wavelengths). The wavelength-versus-transmittance characteristic A of the exciter filter 39 and the wavelength-versus-transmittance characteristic B of the barrier filter 32 are identical to those in the previous embodiment shown in FIG. 2. Incidentally, a mechanism for inserting the barrier filter 32 (third filter) into the optical path or displacing it therefrom is included for enabling selection of insertion or displacement.

Figure 7:
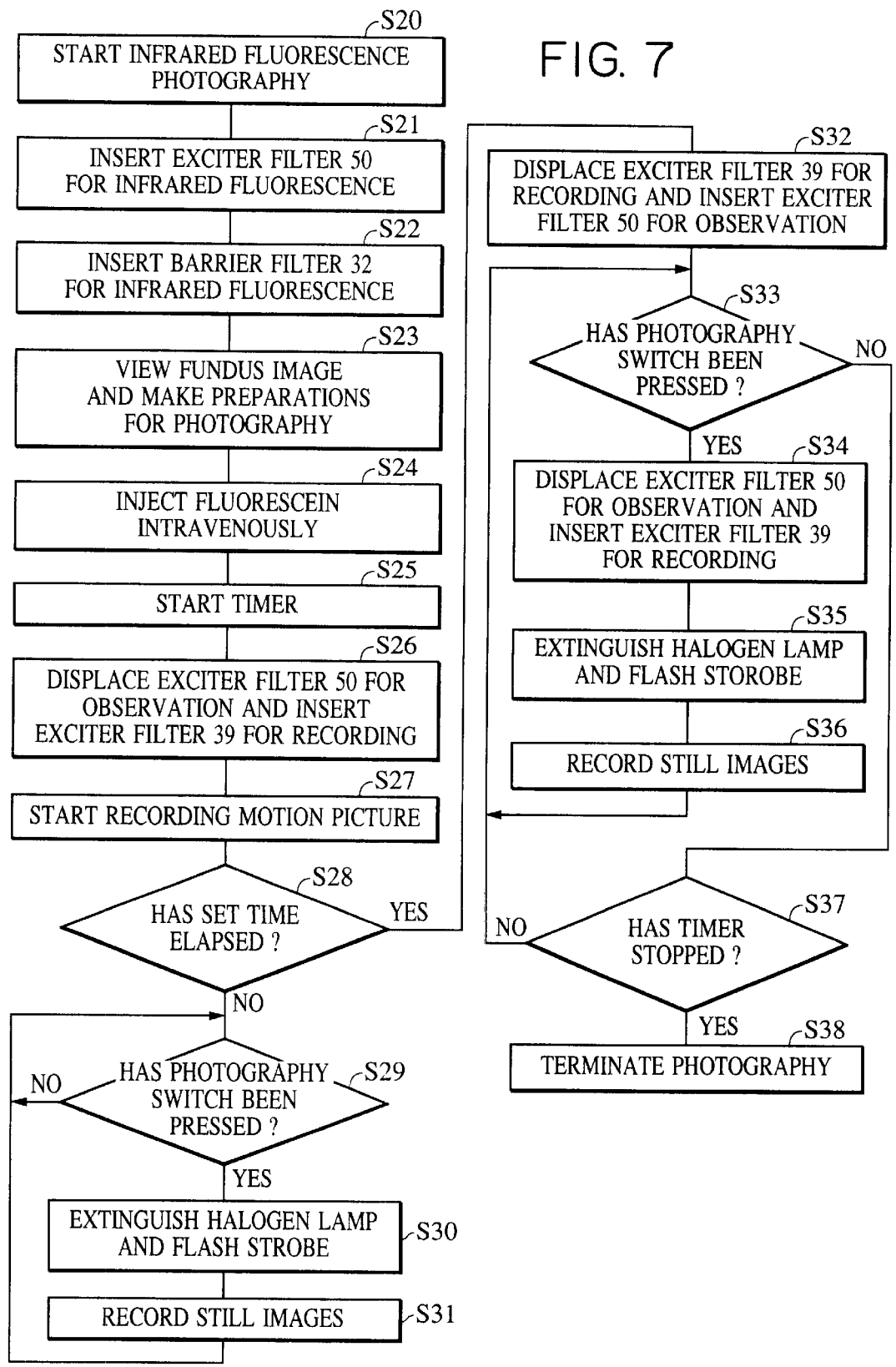
FIG. 7 is a flowchart.

FIG. 7 is a flowchart describing a photography procedure. The barrier filter 32 is displaced out of the optical path O4 for ordinary photography. For infrared fluorescence photography, the barrier filter 32 is inserted into the optical path O4. For observation, the exciter filter 50 is inserted into the optical path O1 and the exciter filter 39 is displaced therefrom. For photographing and recording a fluorescence image, the exciter filter 39 for infrared fluorescence recording is inserted into the optical path O1 and the exciter filter 50 for observation is displaced therefrom. Moreover, for photographing the fluorescence image as still images under strobe light, an operator presses the photography switch 27. The controller 20 then causes the strobe to flash with the exciter filter 39 inserted into the optical path O1.

For recording a fluorescence image, the exciter filter 50 need not always be displaced from the optical path O1. This is because even when the exciter filters 50 (characteristic D) and 39 (characteristic A) are inserted in layers into the optical path O1, light of wavelengths falling within the hatched range in FIG. 6 and being used for observation is intercepted due to a combination of their characteristics. Consequently, the fluorescence image is recorded successfully. In this case, if the exciter filter 50 is interposed between the halogen lamp 37 and strobe 38, the loss in an amount of light for photography caused by the exciter filter 50 will not occur during photography.

For infrared fluorescence photography, which is started in step S20, the exciter filter 50 is inserted into the optical path O1 in step S21. A patient is asked to take a seat. The patient's face is locked in the face holder 22 so that the patient's eye E will be opposed to the objective 42. An operator moves the stage 24 using the position adjustment lever 26 so as to align the optical path O2 substantially with the patient's eye E. The switching mirror 44 is displaced from and out of the optical path O3 and located at a position indicated with a dashed line in FIG. 5. The barrier filter 32 is inserted into the optical path O4 in step S22.

Light emanating from the halogen lamp 37 passes through the exciter filter 39 and is reflected by the mirror 40 to the perforated mirror 41, which reflects the light to the eye E to illuminate the fundus Er of the patient's eye through the objective 42. The light reflected from the fundus passes through the objective 42 and the hole in the perforated mirror 41 to reach the light splitting mirror 43, which reflects the light to the mirror 45. Mirror 45 reflects the light through the barrier filter 32 into the infrared camera 34. A fundus image Er' formed with light of wavelengths permitted to pass through the various filters (wavelengths in the hatched region shown in FIG. 6) is displayed on the display 36 and is viewed by the operator in step S23.

After photography preparations are completed, a fluorescein is intravenously injected into the patient in step S24. The operator presses the timer switch 28 to start the timer 28a in step S25. Then, in step S26, the controller 20 controls the filters to displace the exciter filter 50 for observation out of the optical path O1 and insert the exciter filter 39 into the optical path O1. The image recording device 35 is then used to start motion picture recording and to record timer information (i.e., the time since the timer wave started) under the control of the controller 20 in step S27. The excitation light that illuminates the fundus Er brings about fluorescence. Consequently, a fluorescence fundus image Er' is displayed on the display 36. The operator can now observe the fundus and the process is recorded in the form of a motion picture. If necessary, the operator can finely adjust the focus of the infrared television camera and adjust the amount of light emanating from the halogen lamp 37 according to a change in the intensity of fluorescence.

In step S28, the controller 20 determines whether the predetermined time set by the timer 28a has elapsed. If not, the controller determines whether the operator has pressed photography switch 27 in step S29. For photographing the fluorescence image as still images while photographing it as a motion picture, the operator presses the photography switch 27. When this occurs, under the control of the controller 20, and while the exciter filter 39 remains inserted into the optical path O1, the halogen lamp 37 is extinguished and the strobe 38 is flashed in step S30. Consequently, still images of the fluorescent fundus image and timer information are recorded in the image recording device 35 in step S31.

When some time elapses after intravenous injection, fluorescence fades away. The fundus image Er' displayed on the display 36 becomes indistinct and indiscernible. The time at which fluorescence fades away can be roughly predicted. The timer 28a is used to monitor the passage of this predetermined time. When the controller 20 determines that this predetermined time has elapsed in step S28, the exciter filter 39 is automatically displaced out of the optical path O1 and the exciter filter 50 is automatically inserted into the optical path O1 in step S32 under the control of the controller 20. The image recording device 35 then stops motion-picture recording. Because of the characteristics of the filters 50 and 32, the fundus image Er' is displayed distinctly on the display 36. The operator then designates a desired region to be photographed while looking at the display 36 and presses the photography switch 27. When the controller 20 determines that this has occurred in step S33 in response to a signal generated responsively to the operator's action, the controller 20 displaces the exciter filter 50 out of the optical path O1 and inserts the exciter filter 39 into the optical path O1 in step S34. The halogen lamp 37 is then extinguished and the strobe 38 is flashed in step S35. Still images of the fluorescent fundus image Er' and timer information are then recorded in the image recording device 35 in step S36. A switch dedicated to switching of filters 38 and 50 may be included for selecting either of these filters for use in response to the time measured by the timer 28a and the use of the photography switch 27.

The process then returns to step S33. If the photography switch 27 is not determined to be pressed by the controller 20, the controller 20 determines in step S37 whether the timer 28a stops measuring the predetermined time. If the controller 20 determines that the timer 28a has not stopped, the process returns to step S33. If the controller determines that the timer 28a has stopped, the process advances to step S38 and controller 20 terminates photography.

Next, a description will be made of a case where an operator stick having a double switch is substituted for the photography switch 27 that is a single switch. Even in the embodiment shown in FIG. 5, the photography switch 27 may be realized with a double switch.

Figure 8:
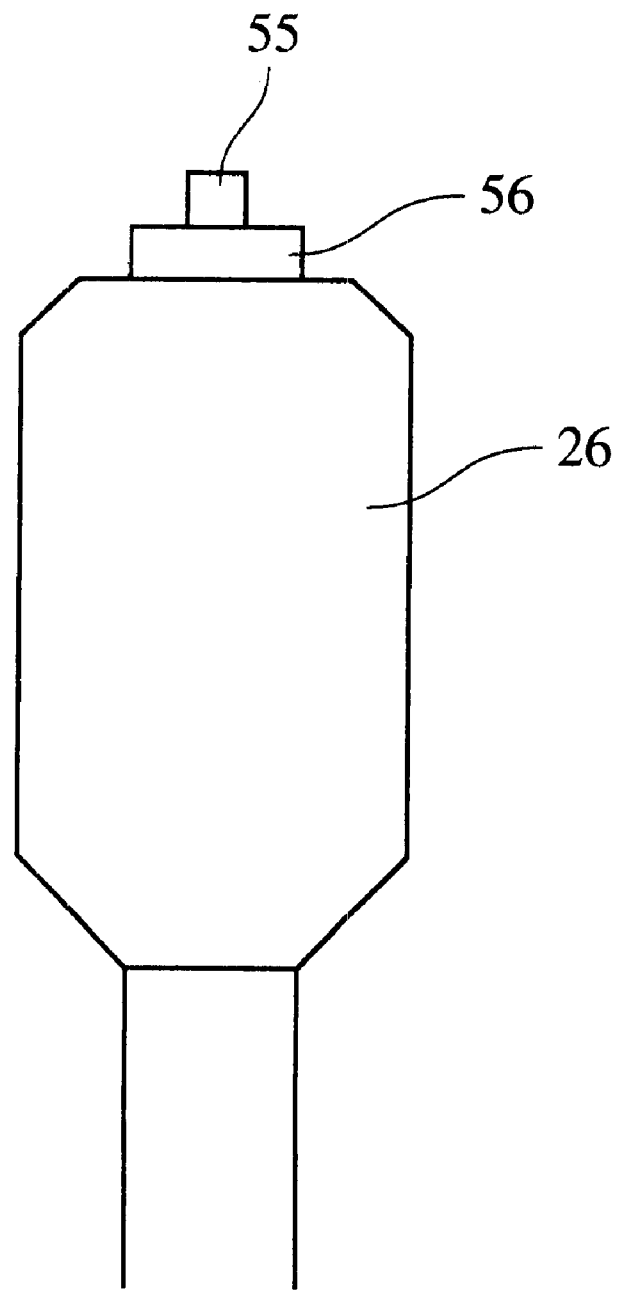
FIG. 8 shows the structure of a double switch.
Figure 9:
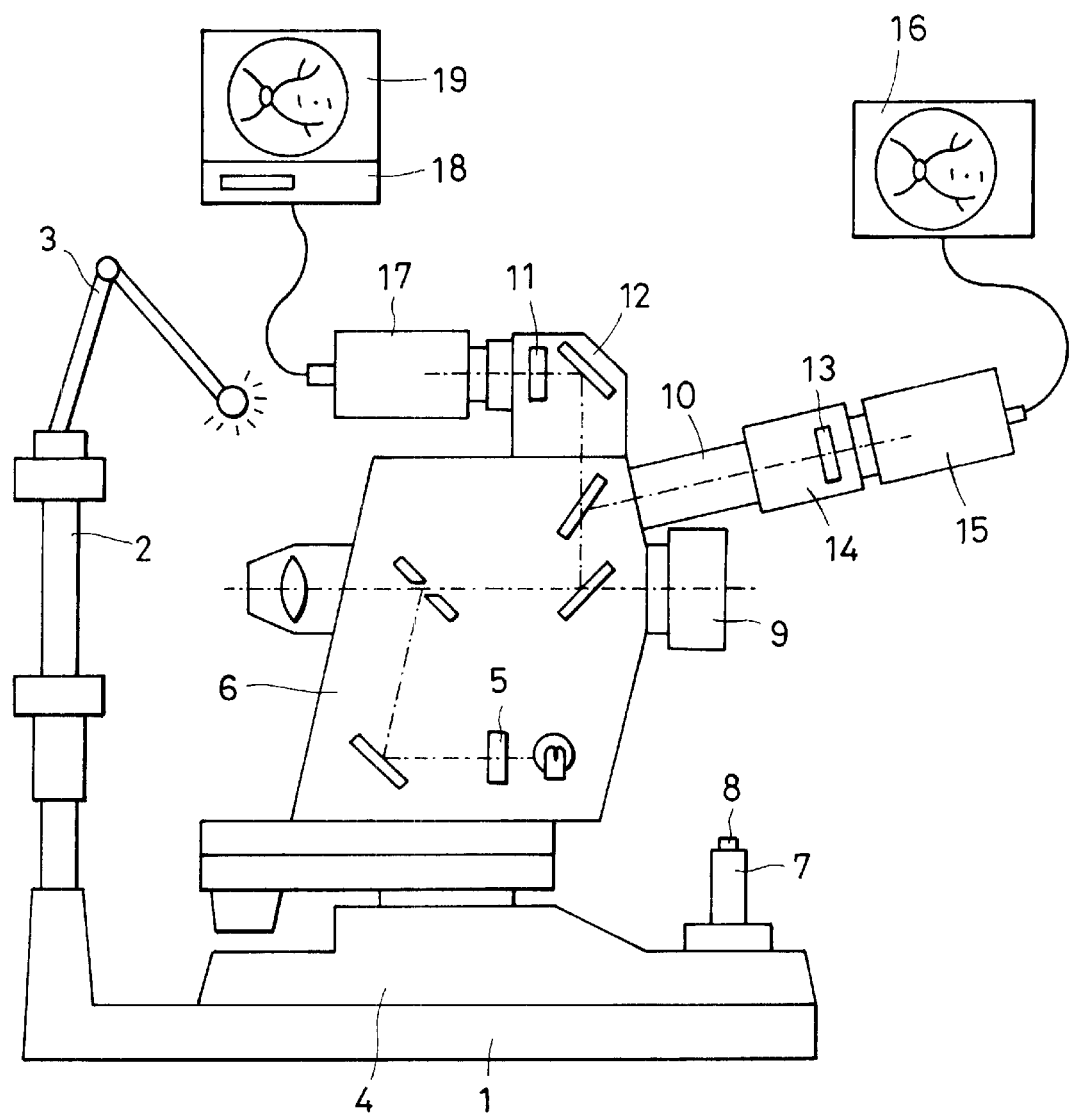
FIG. 9 shows the configuration of a typical eye fundus camera in accordance with a related art.

FIG. 8 is a sectional view of an operator stick. The operator stick has a double switch (first-step switch 55 and second-step switch 56) composed of two switches that are turned on in order depending on a pressing force. In the FIG. 1 embodiment, when the first-step switch 55 is pressed, the controller 20 inserts the barrier filter 33 into the optical path O4. Otherwise, the barrier filter 32 is inserted into the optical path O4.

Preparations including alignment and focusing are made for photography at the sight of a fundus image Er' displayed on the display 36 by the infrared television camera 34. At this time, an operator presses the first-step switch 55 alone with a feeble or small pressing force. When the preparations for photography are completed, a fluorescein is intravenously injected into a patient. The timer switch 28 is pressed to start the timer 28a. The operator then releases the pressed switch 55. The controller 20 inserts the barrier filter 32 into the optical path O4 in place of the barrier filter 33. The image recording device 35 is used to start recording a motion picture and timer information. Fluorescence occurs in due course. A fluorescence fundus image Er' of the patient's eye is then displayed on the display 36. Thereafter, a motion picture is recorded according to a procedure identical to the aforesaid one.

For recording still images, the operator presses the switch with a strong pressing force to turn on both the first-step switch 55 and second-step switch 56. In response to a signal generated responsively to the operator's action, the controller 20 extinguishes the halogen lamp 37 and flashes the strobe 38. Still images of the fluorescence fundus image Er' and timer information are then recorded in the image recording device 35. A time T from the instant the switch 55 is pressed to the instant the switch 56 is pressed is measured. If the time T is smaller than a preset value t, or if T<t, the barrier filter 33 is not inserted into the optical path O4 but the barrier filter 32 is inserted. In other words, for using the barrier filter 32 to photograph a fundus in the form of still images during recording of a motion picture, the switch 55 and switch 56 should be pressed nearly simultaneously during the time T<t. The barrier filter 32 remains inserted into the optical path O4. Thus, the cumbersome switching of the filters is avoided.

When a certain time elapses after intravenous injection, fluorescence fades away. At this time, the operator presses the first-step switch 55 alone so that the barrier filter 33 for observation will be inserted into the optical path O4. Consequently, not only light stemming from fluorescence but also light of wavelengths falling within the hatched range in FIG. 2 reaches the infrared television camera 34. The fundus image Er' is displayed on the display 36. In this state, for recording still images of the fundus image, the operator should merely press both the switch 55 and switch 56.

In the aforesaid eye fundus camera suitable for fluorescence photography of a fundus, the two filters are selectively included in the photography optical system or illumination optical system in order to select a wavelength band. The infrared television camera and display can therefore be used in common for recording and observation. Consequently, the eye fundus camera has a simpler structure and a smaller number of parts than a conventional one, and is compact and low-cost. Moreover, for performing color photography or visible-light fluorescence photography, the optical finder can be utilized without the labor of attaching or detaching a relay lens. The number of cables each required for connection of an infrared television camera can be decreased. This leads to improved maneuverability.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An eye fundus camera comprising:

an illumination optical system configured to illuminate the fundus of a patient's eye with light of wavelengths falling within a first wavelength band;

a photography optical system configured and positioned to form an image of the fundus illuminated by said illumination optical system so that a fundus image will be produced by said camera, said photography optical system including a first filter that exhibits a spectral characteristic of intercepting light of wavelengths falling within the first wavelength band and transmitting light of wavelengths falling within a second wavelength band of longer wavelengths than the first wavelength band, and a second filter which exhibits a spectral characteristic of transmitting light of wavelengths falling within a wavelength band that covers the second wavelength band and includes part of the first wavelength band and that is therefore wider than the second wavelength band including the wavelengths of the light transmitted by said first filter, at least said first filter being capable of being inserted into an optical path of said photography optical system and displaced therefrom;

a photography switch with which an operator gives instructions to photograph the fundus image as still images under strobe light;

a controller for causing a strobe to produce the strobe light when said photography switch is pressed and said first filter is inserted into the optical path; and a display for displaying the fundus image produced by said photography optical system.

2. An eye fundus camera according to claim 1, wherein said illumination optical system includes an exciter filter that exhibits a spectral characteristic of transmitting light of wavelengths falling within the first wavelength band and intercepting light of wavelengths falling within the second wavelength band, and that is displaceable from the optical path.

3. An eye fundus camera according to claim 1, wherein for enabling observation, said controller causes said first filter to be displaced from the optical path and causes said second filter to be inserted thereinto, and wherein for enabling photography, said controller causes said first filter to be inserted into the optical path.

4. An eye fundus camera according to claim 1, wherein said photography switch comprises a double switch, and said controller controls insertion of said second filter in response to pressing of a first-step switch of said double switch, and controls flashing of the strobe light in response to pressing of a second-step switch thereof.

5. An eye fundus camera according to claim 4, wherein when the time interval between the pressing of said first-step switch and the pressing of said second-step switch is smaller than a predetermined value, said controller disables insertion of said second filter.

6. An eye fundus camera according to claim 1, wherein said eye fundus camera enables fluorescence photography of an eye fundus with fluorescein, the first wavelength band includes wavelengths suitable for excitation of the fluorescein, and the second wavelength band includes wavelengths of light produced by fluorescence of the excited fluorescein.

7. An eye fundus camera comprising:

an illumination optical system for illuminating a fundus of a patient's eye, said illumination optical system including a first filter that exhibits a spectral characteristic of transmitting light of wavelengths falling within a first wavelength band and intercepting light of wavelengths falling within a second wavelength band of longer wavelengths than the first wavelength band, and a second filter which exhibits a spectral characteristic of transmitting light of wavelengths falling within a wavelength band that covers the first wavelength band and includes part of the second wavelength band and that is therefore wider than the first wavelength band including the wavelengths of the light transmitted by said first filter, and at least said first filter being capable of being inserted into an optical path of said illumination optical system and displaced therefrom;

a photography optical system for forming an image of a fundus illuminated by said illumination optical system so that the fundus image will be produced by the photography optical system, said photography optical system including a third filter that exhibits a spectral characteristic of intercepting light of wavelengths falling within the first wavelength band and transmitting light of wavelengths falling within the second wavelength band; and a display for displaying the fundus image produced by said photography optical system.

8. An eye fundus camera according to claim 7, further comprising a controller for enabling observation by causing said first filter to be displaced from the optical path and causing said second filter to be inserted into the optical path, and for enabling photography by causing said first filter to be inserted into the optical path.

9. An eye fundus camera according to claim 8, further comprising:

a photography switch with which an operator instructs said camera to photograph the fundus image as still images under strobe light; and a controller for, when said photography switch is pressed, causing a strobe to produce the strobe light with said first filter inserted into the optical path.

10. An eye fundus camera according to claim 9, wherein said photography switch comprises a double switch, and said controller causes said second filter to be inserted into the optical path in response to pressing of a first-step switch of said double switch, and causes the strobe to produce the strobe light in response to pressing of a second-step switch thereof.

11. An eye fundus camera according to claim 8, wherein said eye fundus camera enables fluorescence photography of a fundus with fluorescein, the first wavelength band includes wavelengths suitable for excitation of the fluorescein, and the second wavelength band includes wavelengths of light produced by the fluorescence of the excited fluorescein.

12. An eye fundus infrared camera suitable for infrared fluorescence photography comprising:

an illumination optical system for illuminating a fundus of a patient's eye with excitation light of wavelengths suitable to fluoresce fluorescein;

a photography optical system for forming an image of the eye fundus illuminated by said illumination optical system so that a fundus image will be produced by the infrared camera, said photography optical system including a first barrier filter that exhibits a spectral characteristic of intercepting the excitation light and transmitting light of wavelengths that are longer than the wavelengths of the excitation light produced by the fluorescence of fluorescein, and a second barrier filter that exhibits a spectral characteristic of transmitting light of wavelengths falling within a wavelength band which covers the wavelengths of the light produced by the fluorescence of fluorescein and includes part of the wavelengths of the excitation light and which is therefore wider than the wavelength band including the wavelengths of the light produced by the fluorescence of fluorescein and being transmitted by said first barrier filter, at least said first barrier filter being capable of being inserted into the optical path of said photography optical system and displaced therefrom;

a photography switch with which an operator instructs the infrared camera to photograph the fundus image as still images under strobe light;

a controller for causing, when said photography switch is pressed, a strobe to produce the strobe light with said first barrier filter inserted into the optical path; and a display for displaying the fluorescence fundus image produced by the infrared camera.

13. An eye fundus infrared camera suitable for fluorescence photography comprising:

an illumination optical system for illuminating a fundus of a patient's eye with excitation light of wavelengths suitable to fluoresce fluorescein, said illumination optical system including a first exciter filter that exhibits a spectral characteristic of transmitting light of wavelengths falling within a first wavelength band and intercepting light of wavelengths that are longer than the wavelengths of the first wavelength band produced by the fluorescence of fluorescein, and a second exciter filter which exhibits a spectral characteristic of transmitting light of wavelengths falling within a wavelength band that covers the wavelengths of the excitation light and includes part of the wavelengths of the light produced by the fluorescence of fluorescein and that is therefore wider than the first wavelength band including the wavelengths of the light transmitted by said first exciter filter, and at least said first exciter filter being capable of being inserted into an optical path of said illumination optical system and displaced therefrom;

a photography optical system for forming an image of the fundus illuminated by said illumination optical system so that the fundus image will be produced by the infrared camera, said photography optical system including a barrier filter that exhibits a spectral characteristic of intercepting the excitation light and transmitting the light produced by the fluorescence of fluorescein; and a display for displaying the fluorescence fundus image produced by said photography optical system.

14. An eye fundus camera according to claim 12 or 13, wherein said fluorescein is indocyanine green.

15. A method of performing fluorescence photography of an eye fundus with an eye fundus camera comprising the steps of:

illuminating the fundus of a patient's eye with light of wavelengths only falling within a first wavelength band;

transmitting light reflected by the fundus only in a portion of the first wavelength band through a photography optical system to an infrared television camera to produce a fundus image;

displaying the fundus image to permit an operator of the fundus camera to align and focus the fundus camera while viewing the displayed fundus image;

measuring the time from injection of a fluorescein into the patient's eye, the fluorescein fluorescing and producing light of wavelengths falling into a second wavelength band in response to being exposed to excitation light in the first wavelength band;

transmitting light only in the second wavelength band from the patient's eye produced by the fluorescing of the fluorescein through the photography optical system to the infrared television camera; and recording a motion picture of the fundus and displaying the fundus image produced by the infrared camera using the light only in the second wavelength band from the patient's eye produced by the fluorescing of the fluorescein.

16. A method according to claim 15, wherein said illuminating step comprises the step of inserting an exciter filter transmitting light of wavelengths only falling within a first wavelength band into the optical path of an illumination optical system;

wherein said first transmitting step comprises the step of inserting a first barrier filter transmitting light only in the portion of the first wavelength band into the optical path of the photography optical system;

wherein said measuring step is performed by starting a timer; and wherein said second transmitting step comprises the step of removing the first barrier filter from the optical path of the photography optical system and inserting a second barrier filter transmitting light of wavelengths only in the second wavelength band into the optical path of the photography optical system.

17. A method according to claim 15 further comprising the steps of:

transmitting light reflected by the fundus only in the portion of the first wavelength band through a photography optical system to the infrared television camera to produce a fundus image using the first-wavelength-band light in response to the elapsing of a predetermined time from the time of injection of a fluorescein into the patient's eye measured in said measuring step;

displaying the fundus image produced using the first-wavelength-band light to permit an operator of the fundus camera to designate a region of the fundus to be photographed;

transmitting light only in the second wavelength band from the patient's eye produced by the fluorescing of the fluorescein through the photography optical system to the infrared television camera in response to a photography switch being pressed by the operator;

stopping said illuminating step, flashing strobe light to illuminate the patient's eye with strobe light, and recording still images of the strobe-illuminated fundus of the patient's eye in response to a photography switch being pressed by the operator;

stopping the measuring operation performed in said measuring step; and terminating the recording of still images in response to the stopping of the measuring operation in said measuring-operation stopping step.

18. A method according to claim 17, wherein said transmitting step performed in response to the elapsing of the predetermined time is performed by displacing said second barrier filter out of the optical path of the photography optical system and inserting the first barrier filter into the optical path of the photography optical system;

wherein said transmitting step of transmitting light only in the second wavelength band in response to a photography switch being pressed by the operator is performed by displacing the first barrier filter out of the optical path of the photography optical system and inserting the second barrier filter into the optical path of the photography optical system.

19. A method according to claim 15, further comprising the steps of:

stopping said illuminating step, flashing strobe light to illuminate the patient's eye with strobe light, and recording still images of the strobe-illuminated fundus of the patient's eye in response to both a determination that a predetermined amount of time has not elapsed from the time of injection of a fluorescein into the patient's eye measured in said measuring step and a photography switch being pressed by the operator.

20. A method of performing fluorescence photography of an eye fundus with an eye fundus camera comprising the steps of:

illuminating the fundus of a patient's eye with light of wavelengths only falling within a first wavelength band and a portion of a second wavelength band of longer wavelengths than the first wavelength band;

transmitting light reflected by the fundus only in the portion of the second wavelength band from a photography optical system to an infrared television camera to produce a fundus image;

displaying the fundus image to permit an operator of the fundus camera to align and focus the fundus camera while viewing the displayed fundus image;

measuring the time from injection of a fluorescein into the patient's eye, the fluorescein fluorescing and producing light of wavelengths falling into the second wavelength band in response to being exposed to excitation light in the first wavelength band;

transmitting light only in the second wavelength band from the patient's eye produced by the fluorescing of the fluorescein from the photography optical system to the infrared television camera; and recording a motion picture of the fundus and displaying the fundus image produced by the infrared camera using the light only in the second wavelength band from the patient's eye produced by the fluorescing of the fluorescein.

21. A method according to claim 20, wherein said illuminating step comprises the step of inserting a first exciter filter transmitting light of wavelengths only falling within a first wavelength band and the portion of the second wavelength band into the optical path of an illumination optical system;

wherein said first transmitting step comprises the step of inserting a barrier filter transmitting light only in the second wavelength band into the optical path of the photography optical system;

wherein said measuring step is performed by starting a timer; and wherein said second transmitting step comprises the step of removing the first exciter filter from the optical path of the illumination optical system and inserting a second exciter filter transmitting light of wavelengths only in the first wavelength band into the optical path of the illumination optical system.

22. A method according to claim 20, further comprising the steps of:

transmitting light reflected by the fundus only in the portion of the second wavelength band from the photography optical system to the infrared television camera to produce a fundus image using the light illuminating the fundus from the illumination optical system in response to the elapsing of a predetermined time from the time of injection of a fluorescein into the patient's eye measured in said measuring step;

displaying the fundus image produced using the light illuminating the fundus from the illumination optical system to permit an operator of the fundus camera to designate a region of the fundus to be photographed;

transmitting light only in the second wavelength band from the patient's eye produced by the fluorescing of the fluorescein from the photography optical system to the infrared television camera in response to a photography switch being pressed by the operator;

stopping said illuminating step, flashing strobe light to illuminate the patient's eye with strobe light, and recording still images of the strobe-illuminated fundus of the patient's eye in response to a photography switch being pressed by the operator;

stopping the measuring operation performed in said measuring step; and terminating the recording of still images in response to the stopping of the measuring operation in said measuring-operation stopping step.

23. A method according to claim 22, wherein said transmitting step performed in response to the elapsing of the predetermined time is performed by displacing said second exciter filter out of the optical path of the illumination optical system and inserting the first exciter filter into the optical path of the illumination optical system;

wherein said transmitting step of transmitting light only in the second wavelength band in response to a photography switch being pressed by the operator is performed by displacing the first exciter filter out of the optical path of the illumination optical system and inserting the second exciter filter into the optical path of the illumination optical system.

24. A method according to claim 20, further comprising the steps of:

stopping said illuminating step, flashing strobe light to illuminate the patient's eye with strobe light, and recording still images of the strobe-illuminated fundus of the patient's eye in response to both a determination that a predetermined amount of time has not elapsed from the time of injection of a fluorescein into the patient's eye measured in said measuring step and a photography switch being pressed by the operator.

25. An eye fundus camera comprising:

means for illuminating the fundus of a patient's eye with light of wavelengths falling within a first wavelength band;

means for forming an image of the fundus illuminated by said illuminating means and for photographing the image, said image forming means including first filter means for intercepting light of wavelengths falling within the first wavelength band and transmitting light of wavelengths falling within a second wavelength band of longer wavelengths than the first wavelength band, and second filter means for transmitting light of wavelengths falling within a wavelength band that covers the second wavelength band and includes part of the first wavelength band and that is therefore wider than the second wavelength band including the wavelengths of the light transmitted by said first filter means, at least said first filter means being capable of being inserted into an optical path of said image forming means and displaced therefrom;

operator-actuated means for instructing the photographing of the fundus image with said image forming means as still images under strobe light;

control means for controlling a strobe to produce the strobe light when said operator-actuated means is actuated and said first filter means is inserted into the optical path; and display means for displaying the fundus image produced by said image forming means.

26. An eye fundus camera according to claim 25, wherein said illuminating means includes exciter filter means for transmitting light of wavelengths falling within the first wavelength band and intercepting light of wavelengths falling within the second wavelength band, and that is displaceable from the optical path.

27. An eye fundus camera according to claim 25, wherein for enabling observation, said control means controls said first filter means to be displaced from the optical path and controls said second filter means to be inserted thereinto, and wherein for enabling photography, said control means controls said first filter means to be inserted into the optical path.

28. An eye fundus camera according to claim 25, wherein said operator-actuated means comprises double instruction means for permitting the operator to input two different instructions into said camera, and wherein said control means controls insertion of said second filter means in response to the operator actuating first instruction means of said double instruction means, and said control means controls flashing of the strobe light in response to the operator actuating second instruction means of said double instruction means.

29. An eye fundus camera according to claim 28, wherein when the time interval between the actuating said first instruction means and actuating said second instruction means is smaller than a predetermined value, said control means disables insertion of said second filter means.

30. An eye fundus camera according to claim 25, wherein said eye fundus camera enables fluorescence photography of an eye fundus with fluorescein, the first wavelength band includes wavelengths suitable for excitation of the fluorescein, and the second wavelength band includes wavelengths of light produced by fluorescence of the excited fluorescein.

31. An eye fundus camera comprising:

illuminating means for illuminating a fundus of a patient's eye, said illuminating means including first filter means for transmitting light of wavelengths falling within a first wavelength band and intercepting light of wavelengths falling within a second wavelength band of longer wavelengths than the first wavelength band, and second filter means for transmitting light of wavelengths falling within a wavelength band that covers the first wavelength band and includes part of the second wavelength band and that is therefore wider than the first wavelength band including the wavelengths of the light transmitted by said first filter means, and at least said first filter means being capable of being inserted into an optical path of said illuminating means and displaced therefrom;

means for forming an image of a fundus illuminated by said illuminating means and photographing the fundus image, said image forming means including third filter means for intercepting light of wavelengths falling within the first wavelength band and transmitting light of wavelengths falling within the second wavelength band; and display means for displaying the fundus image produced by said image forming means.

32. An eye fundus camera according to claim 31, further comprising control means for enabling observation by controlling said first filter means to be displaced from the optical path and controlling said second filter means to be inserted into the optical path, and for enabling photography by controlling said first filter means to be inserted into the optical path.

33. An eye fundus camera according to claim 32, further comprising:

operator-actuated means for instructing said camera to photograph the fundus image as still images under strobe light; and control means for, when said operator-actuated means is actuated by the operator, controlling a strobe to produce the strobe light with said first filter means inserted into the optical path.

34. An eye fundus camera according to claim 33, wherein said operator-actuated means comprises double instruction means for permitting the operator to input two different instructions into said camera, and said control means controls said second filter means to be inserted into the optical path in response to the operator actuating first instruction means of said double instruction means, and controls the strobe to produce the strobe light in response to the operator actuating second instruction means of said double instruction means.

35. An eye fundus camera according to claim 32, wherein said eye fundus camera enables fluorescence photography of a fundus with fluorescein, the first wavelength band includes wavelengths suitable for excitation of the fluorescein, and the second wavelength band includes wavelengths of light produced by the fluorescence of the excited fluorescein.

36. An eye fundus infrared camera suitable for infrared fluorescence photography comprising:

illuminating means for illuminating a fundus of a patient's eye with excitation light of wavelengths suitable to fluoresce fluorescein;

means for forming an image of the eye fundus illuminated by said illuminating means and photographing the fundus image, said image forming means including first barrier filter means for intercepting the excitation light and transmitting light of wavelengths that are longer than the wavelengths of the excitation light produced by the fluorescence of fluorescein, and second barrier filter means for transmitting light of wavelengths falling within a wavelength band that covers the wavelengths of the light produced by the fluorescence of fluorescein and includes part of the wavelengths of the excitation light and that is therefore wider than the wavelength band including the wavelengths of the light produced by the fluorescence of fluorescein and being transmitted by said first barrier filter means, at least said first barrier filter means being capable of being inserted into the optical path of said photography optical system and displaced therefrom;

operator-actuated means for instructing the photographing of the fundus image with said image forming means as still images under strobe light;

control means for causing, when said operator-actuated means is actuated, a strobe to produce the strobe light with said first barrier filter means inserted into the optical path; and display means for displaying the fluorescence fundus image produced by the infrared camera.

37. An eye fundus infrared camera suitable for fluorescence photography comprising:

illuminating means for illuminating a fundus of a patient's eye with excitation light of wavelengths suitable to fluoresce fluorescein, said illuminating means including first exciter filter means for transmitting light of wavelengths falling within a first wavelength band and intercepting light of wavelengths that are longer than the wavelengths of the first wavelength band produced by the fluorescence of fluorescein, and second exciter filter means for transmitting light of wavelengths falling within a wavelength band that covers the wavelengths of the excitation light and includes part of the wavelengths of the light produced by the fluorescence of fluorescein and that is therefore wider than the first wavelength band including the wavelengths of the light transmitted by said first exciter filter means, and at least said first exciter filter means being capable of being inserted into an optical path of said illuminating means and displaced therefrom;

means for forming an image of the fundus illuminated by said illuminating means and photographing the fungus image, said image forming means including barrier filter means for intercepting the excitation light and transmitting the light produced by the fluorescence of fluorescein; and display means for displaying the fluorescence fundus image produced by said image forming means.

38. An eye fundus camera according to claim 36 or 37, wherein said fluorescein is indocyanine green.

* * * * *

UNITED STATES PATENT AND TRADEMARK OFFICE
CERTIFICATE OF CORRECTION

PATENT NO. : 6,456,787 B1
DATED : September 24, 2002
INVENTOR(S) : Kazuhiro Matsumoto et al.

It is certified that error appears in the above-identified patent and that said Letters Patent is hereby corrected as shown below:

<u>Column 2,</u>
Line 2, "lend" should read -- lens --.

<u>Column 9,</u>
Line 8, "with-excitation" should read -- with excitation --.

<u>Column 12,</u>
Line 40, "finely" should read -- can finely --.

<u>Column 26,</u>
Line 11, "fungus" should read -- fundus --.

Signed and Sealed this

Eighteenth Day of February, 2003

JAMES E. ROGAN
*Director of the United States Patent and Trademark Office*